(12) United States Patent
Lee et al.

(10) Patent No.: US 9,254,471 B2
(45) Date of Patent: Feb. 9, 2016

(54) APPARATUS AND METHOD FOR SYNTHESIZING F-18 LABELED RADIOACTIVE PHARMACEUTICALS

(75) Inventors: Cheol-Soo Lee, Seoul (KR); Dae-Yoon Chi, Seoul (KR); Eun-Young Heo, Jeonbuk (KR); Jong-Min Kim, Seoul (KR); Byoung-Se Lee, Incheon (KR); Hee-Seup Kil, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 0 days.

(21) Appl. No.: 14/117,622

(22) PCT Filed: May 11, 2012

(86) PCT No.: PCT/KR2012/003706
§ 371 (c)(1),
(2), (4) Date: Nov. 13, 2013

(87) PCT Pub. No.: WO2012/157898
PCT Pub. Date: Nov. 22, 2012

(65) Prior Publication Data
US 2015/0087868 A1    Mar. 26, 2015

(30) Foreign Application Priority Data
May 13, 2011   (KR) .................. 10-2011-0045388

(51) Int. Cl.
| | |
|---|---|
| *B01J 19/00* | (2006.01) |
| *C07B 59/00* | (2006.01) |
| *A61J 3/00* | (2006.01) |
| G21G 1/00 | (2006.01) |
| A61J 1/20 | (2006.01) |
| B65B 3/00 | (2006.01) |

(52) U.S. Cl.
CPC ............. *B01J 19/004* (2013.01); *A61J 3/002* (2013.01); *C07B 59/00* (2013.01); *A61J 1/2037* (2013.01); *A61J 1/2089* (2013.01); *B01J 2219/00054* (2013.01); *B01J 2219/00164* (2013.01); *B65B 3/003* (2013.01); *G21G 1/0005* (2013.01)

(58) Field of Classification Search
CPC ................... B01J 19/004; B01J 2219/00054; B01J 2219/00164; C07B 59/00
See application file for complete search history.

(56) References Cited

U.S. PATENT DOCUMENTS 5,932,178 A * 8/1999 Yamazaki et al. ............ 422/159
7,714,115 B2 * 5/2010 Grigg et al. .................. 536/18.4

FOREIGN PATENT DOCUMENTS

| JP | H09-263594 A | 10/1997 |
| JP | 2008-515793 A | 5/2008 |
| JP | 2009-165597 A | 7/2009 |
| KR | 2008-0078233 A | 8/2008 |

* cited by examiner

*Primary Examiner* — Shailendra Kumar
(74) *Attorney, Agent, or Firm* — Rabin & Berdo, P.C.

(57) ABSTRACT

Method and apparatus for synthesizing an F-18 labeled radioactive pharmaceutical by labeling a precursor with an F-18 radioactive isotope, by reacting the labeled precursor to obtain a labeled pharmaceutical, by separating impurities from the labeled pharmaceutical to provide a purified labeled pharmaceutical, and by collecting the purified labeled pharmaceutical. The apparatus includes a labeling cartridge that contains the precursor, receives the isotope, and causes a labeling reaction to provide the labeled precursor; a synthesizing container that receives the labeled precursor, receives at least one reagent effective to hydrolyze the labeled precursor, and within which the labeled precursor undergoes a hydrolysis reaction to provide the labeled pharmaceutical; and a separation cartridge that receives the labeled pharmaceutical, and contains a polymer compound that separates impurities into polar compounds and nonpolar compounds to provide the purified labeled pharmaceutical. The labeling and separation cartridges may be contained in a removable cassette.

17 Claims, 3 Drawing Sheets

APPARATUS AND METHOD FOR SYNTHESIZING F-18 LABELED RADIOACTIVE PHARMACEUTICALS

This application is a 371 of PCT/KR2012/003706, filed on May 11, 2012.

TECHNICAL FIELD

The present invention relates to an apparatus and method for synthesizing F-18 labeled radioactive pharmaceutical.

BACKGROUND ART

Synthesis of radioactive pharmaceutical having short half-life is performed by an apparatus in which a radioactive isotope and a reagent are reacted together and the obtained product material is purified. Certain parts comprising such an apparatus may be sensitive to radioactivity or chemical corrosion.

Synthesis of radioactive pharmaceutical for PET (positron emission tomography) which is an example of radioactive pharmaceuticals is performed by labeling a radioactive isotope which is formed by a cyclotron onto a precursor. An automatic synthesizing apparatus is inevitable for such a synthesis, and since a radiation is emitted continuously during synthesizing process it is impossible to synthesize manually by a person.

However, since a conventional radioactive pharmaceutical synthesizing apparatus has a complicated synthesizing process, there is a problem in that it is hard to expect a high yield and radiation exposure of a worker may be increased. In addition, a specific apparatus for a specific radioactive pharmaceutical designed to obtain a certain purpose cannot support various kinds of radioactive pharmaceutical and there is a limitation in applying such apparatus to development of a various new medicines.

DETAILED DESCRIPTION OF THE INVENTION

Technical Problem

The present invention has been made in an effort to provide an apparatus and method for synthesizing F-18 labeled radioactive pharmaceutical which adopts a type of removeable cassette using a polymer precursor cartridge and can automatically performs synthesis of radioactive pharmaceuticals.

Technical Solution

An apparatus for synthesizing F-18 labeled radioactive pharmaceutical according to an exemplary embodiment of the present invention includes: an F-18 radioactive isotope supplier which supplies F-18 radioactive isotope; a reagent supplier which supplies reagent reacting with the F-18 radioactive isotope; a polymer precursor cartridge which is filled with polymer precursor and collects the F-18 radioactive isotope and causes a labeling reaction; a first heating unit which selectively heats the polymer precursor cartridge; a polymer compound cartridge which is filled with polymer compound and separates polar compound and nonpolar compound from each other; a synthesizing container which causes hydrolysis reaction of produced intermediate compound; a second heating unit which selectively heats the synthesizing container; a waste liquid container which contains fluid which is discarded after having been used for synthesis; a collecting container which collects a final synthesized product; a transmitting gas supplier which supplies transmitting gas; a cleansing liquid supplier which supplies a cleansing liquid; a connection tube which connects the F-18 radioactive isotope supplier, the reagent supplier, the polymer precursor cartridge, the polymer compound cartridge, the synthesizing container, the waste liquid container, the collection container, the transmitting gas supplier, and the cleansing liquid supplier together; a plurality of control valves which are disposed at predetermined positions of the connection tube to perform selective opening and closing operations; and a controller which controls operations of the first heating unit, the second heating unit and the plurality of the control valves.

The reagent supplier may include: a first organic solvent supplying unit which supplies first organic solvent for removing water within the polymer precursor cartridge; a second organic solvent supplying unit which supplies second organic solvent which is an organic solvent containing acid or a mixed liquid of water and organic solvent to be able to be used as a reaction solvent for elution and deprotection of F-18 labeled compound produced within the polymer precursor cartridge; an alkaline aqueous solution supplying unit which supplies an alkaline aqueous solution for neutralizing synthesized liquid within the synthesizing container; and a third organic solvent supplying unit which supplies a third organic solvent for elution of F-18 labeled compound within the polymer compound cartridge.

The polymer precursor may be a polymer precursor which is connected by quaternary ammonium salt.

The apparatus may further include a vacuum pump which is connected to the waste container, the synthesizing container and the collection container to selectively form vacuum therein to provide power to transmit one or more of the F-18 radioactive isotope, the transmitting gas, the cleansing liquid and the reagent.

The polymer precursor cartridge, the polymer compound cartridge, the connection tube, and the plurality of the control valves may be formed in a type of a removeable cassette which can be selectively attached or detached.

The controller may control the plurality of the control valves, the first heating unit, and the second heating unit so as to sequentially perform: making F-18 radioactive isotope pass through the polymer precursor cartridge and then flow into the waste liquid container; making the transmitting gas pass through the polymer precursor cartridge and then flow into the waster liquid container; making the cleaning liquid pass through the polymer precursor cartridge and then flow into the waster liquid container; making the first organic solvent pass through the polymer precursor cartridge and then flow into the waster liquid container; closing the connection tube connected to the polymer precursor cartridge; heating the polymer precursor cartridge using the first heating unit; making the transmitting gas pass through the polymer precursor cartridge so as to cool the polymer precursor cartridge; making the second organic solvent pass through the polymer precursor cartridge and then flow into the synthesizing container; heating the synthesizing container using the second heating unit; making the alkaline liquid flow into the synthesizing container; making liquid within the synthesizing container pass through the polymer compound cartridge and then flow into the waste liquid container; making the cleansing liquid pass through the polymer compound cartridge and then flow into the waste liquid container; making the transmitting gas pass through the polymer compound cartridge and then flow into the waste liquid container; and making the third organic solvent pass through the polymer compound cartridge and then flow into the collection container.

The controller may control the plurality of the control valves and the first heating unit so as to sequentially perform: making F-18 radioactive isotope pass through the polymer precursor cartridge and then flow into the waste liquid container; making the transmitting gas pass through the polymer precursor cartridge and then flow into the waster liquid container; making the cleaning liquid pass through the polymer precursor cartridge and then flow into the waster liquid container; making the first organic solvent pass through the polymer precursor cartridge and then flow into the waster liquid container; closing the connection tube connected to the polymer precursor cartridge; heating the polymer precursor cartridge using the first heating unit; making the transmitting gas pass through the polymer precursor cartridge so as to cool the polymer precursor cartridge; and making the third organic solvent pass through the polymer compound cartridge and then flow into the collection container.

The controller may control the plurality of the control valves, the first heating unit, and the second heating unit so as to sequentially perform: making F-18 radioactive isotope pass through the polymer precursor cartridge and then flow into the waste liquid container; making the transmitting gas pass through the polymer precursor cartridge and then flow into the waster liquid container; making the cleaning liquid pass through the polymer precursor cartridge and then flow into the waster liquid container; making the first organic solvent pass through the polymer precursor cartridge and then flow into the waster liquid container; closing the connection tube connected to the polymer precursor cartridge; heating the polymer precursor cartridge using the first heating unit; making the transmitting gas pass through the polymer precursor cartridge so as to cool the polymer precursor cartridge; making the second organic solvent sequentially pass through the polymer precursor cartridge and the polymer compound cartridge and then flow into the synthesizing container; making the transmitting gas sequentially pass through the polymer precursor cartridge and the polymer compound cartridge and then flow into the waste liquid container; and making the third organic solvent pass through the polymer compound cartridge and then flow into the collection container.

According to an explary embodiment of the present invention, a method for synthesizing radioactive pharmaceutical using an apparatus for synthesizing radioactive pharmaceutical including a polymer precursor cartridge which is filled with polymer precursor and collects F-18 radioactive isotope to cause a labeling reaction, a polymer compound cartridge which is filled with polymer compound and separates polar compound and nonpolar compound from each other, a synthesizing container which causes hydrolysis reaction of produced intermediate compound, a waste liquid container which contains the produced intermediate compound, a collection container which collects final synthesized product, and a connection tube which connects the polymer precursor cartridge, the polymer compound cartridge, the synthesizing container, the waste liquid container, and the collection container together, includes: making F-18 radioactive isotope pass through the polymer precursor cartridge and then flow into the waste liquid container; making the transmitting gas pass through the polymer precursor cartridge and then flow into the waster liquid container; making the cleaning liquid pass through the polymer precursor cartridge and then flow into the waster liquid container; making the first organic solvent pass through the polymer precursor cartridge and then flow into the waster liquid container; closing the connection tube connected to the polymer precursor cartridge; heating the polymer precursor cartridge using the first heating unit; making the transmitting gas pass through the polymer precursor cartridge so as to cool the polymer precursor cartridge; making the second organic solvent pass through the polymer precursor cartridge and then flow into the synthesizing container; heating the synthesizing container using the second heating unit; making the alkaline liquid flow into the synthesizing container; making liquid within the synthesizing container pass through the polymer compound cartridge and then flow into the waste liquid container; making the cleansing liquid pass through the polymer compound cartridge and then flow into the waste liquid container; making the transmitting gas pass through the polymer compound cartridge and then flow into the waste liquid container; and making the third organic solvent pass through the polymer compound cartridge and then flow into the collection container.

According to another explary embodiment of the present invention, a method for synthesizing radioactive pharmaceutical using an apparatus for synthesizing radioactive pharmaceutical including a polymer precursor cartridge which is filled with polymer precursor and collects F-18 radioactive isotope to cause a labeling reaction, a polymer compound cartridge which is filled with polymer compound and separates polar compound and nonpolar compound from each other, a synthesizing container which collects produced compound and causes hydrolysis reaction, a waste liquid container which contains produced intermediate compound, a collection container which collects final synthesized product, and a connection tube which connects the polymer precursor cartridge, the polymer compound cartridge, the synthesizing container, the waste liquid container, and the collection container together, includes: making F-18 radioactive isotope pass through the polymer precursor cartridge and then flow into the waste liquid container; making the transmitting gas pass through the polymer precursor cartridge and then flow into the waster liquid container; making the cleaning liquid pass through the polymer precursor cartridge and then flow into the waster liquid container; making the first organic solvent pass through the polymer precursor cartridge and then flow into the waster liquid container; closing the connection tube connected to the polymer precursor cartridge; heating the polymer precursor cartridge using the first heating unit; making the transmitting gas pass through the polymer precursor cartridge so as to cool the polymer precursor cartridge; and making the third organic solvent pass through the polymer compound cartridge and then flow into the collection container.

According to another explary embodiment of the present invention, a method for synthesizing radioactive pharmaceutical using an apparatus for synthesizing radioactive pharmaceutical including a polymer precursor cartridge which is filled with polymer precursor and collects F-18 radioactive isotope to cause a labeling reaction, a polymer compound cartridge which is filled with polymer compound and separates polar compound and nonpolar compound from each other, a synthesizing container which causes hydrolysis reaction of produced intermediate compound, a waste liquid container which contains the produced intermediate compound, a collection container which collects final synthesized product, and a connection tube which connects the polymer precursor cartridge, the polymer compound cartridge, the synthesizing container, the waste liquid container, and the collection container together, includes: making F-18 radioactive isotope pass through the polymer precursor cartridge and then flow into the waste liquid container; making the transmitting gas pass through the polymer precursor cartridge and then flow into the waster liquid container; making the cleaning liquid pass through the polymer precursor cartridge and then flow into the waster liquid container; making the first organic solvent pass through the polymer precursor cartridge and then flow into the waster liquid container; closing the connection tube connected to the polymer precursor cartridge; heating the polymer precursor cartridge using the first heating unit; making the transmitting gas pass through the polymer precursor cartridge so as to cool the polymer precursor cartridge; making the second organic solvent sequentially pass through the polymer precursor cartridge and the polymer compound cartridge and then flow into the synthesizing container; making the transmitting gas sequentially pass through the polymer precursor cartridge and the polymer compound cartridge and then flow into the waste liquid container; and making the third organic solvent pass through the polymer compound cartridge and then flow into the collection container.

Advantageous Effects

According to the present invention, the synthesis of radioactive pharmaceutical can be automatically performed by a single removeable cassette and a controller.

DETAILED DESCRIPTION OF THE EMBODIMENTS

Embodiments of the present invention will be explained with reference to the accompanied drawings hereinafter.

A radioactive pharmaceutical synthesis apparatus according to an embodiment of the present invention can automatically synthesize F-18 labeled radioactive pharmaceutical, so a worker can be protected from radiation exposure.

Figure 1:
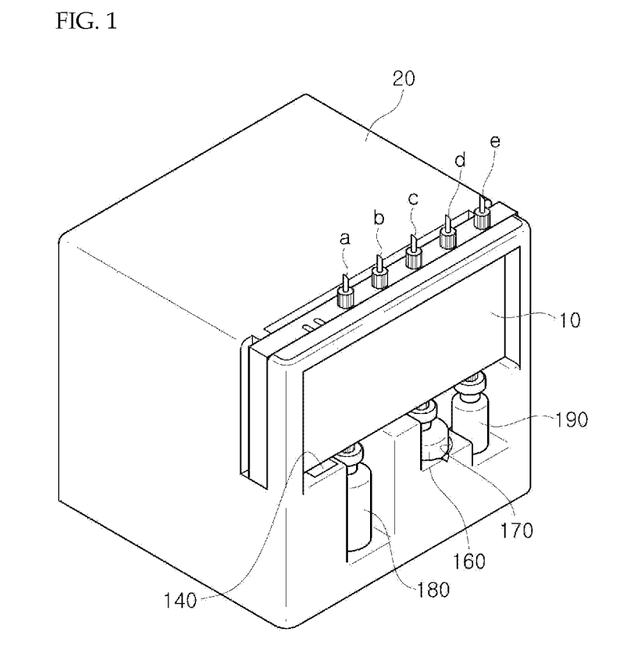
FIG. 1 is a schematic perspective view of an apparatus for synthesizing radiopharmaceutical according to an embodiment of the present invention.

Exemplarily, referring to FIG. 1, an apparatus for synthesizing F-18 labeled radioactive pharmaceutical may include a removeable cassette 10 and a body 20. The cassette 10 may be configured to be attached to the body 20 and to be detached from the body 20, and the cassette 10 may be formed for a single use and the body 20 may be used repeatedly. Some components of the apparatus for synthesizing F-18 labeled radioactive pharmaceutical may be provided within the cassette 10 and the other components thereof may be provided within the body 20.

Figure 2:
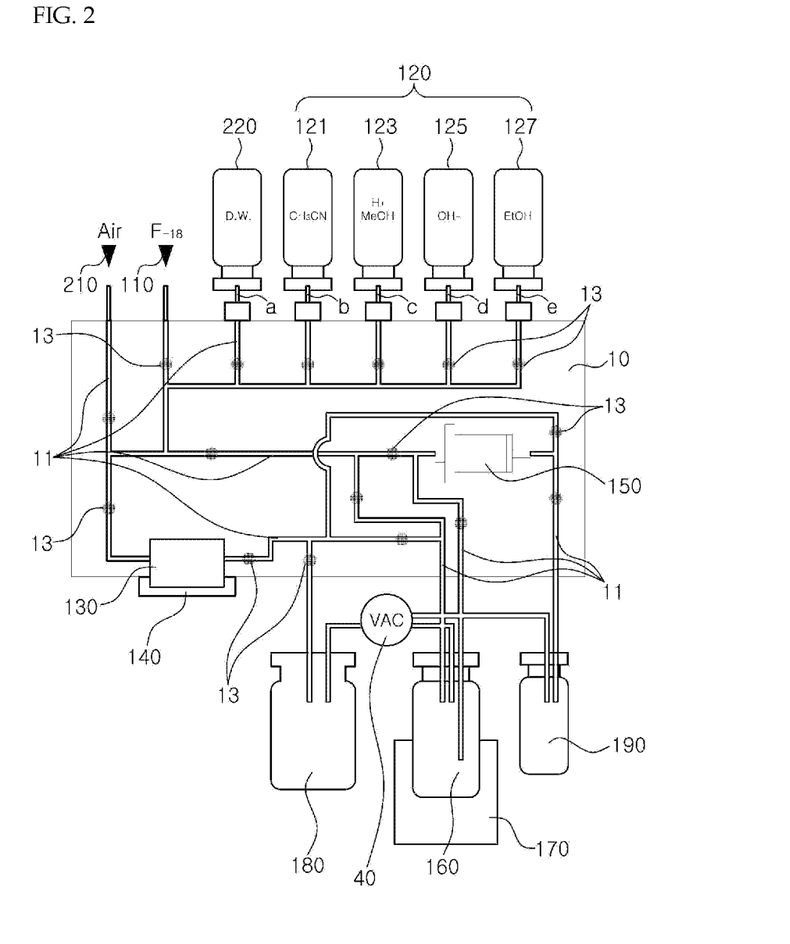
FIG. 2 is a drawing schematically showing components of an apparatus for synthesizing radiopharmaceutical according to an embodiment of the present invention.
Figure 3:
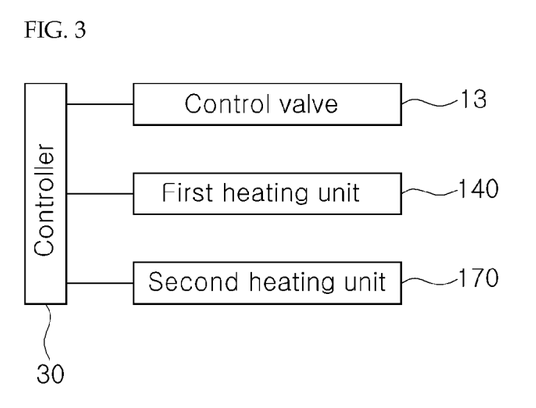
FIG. 3 is a block diagram showing a controller and related control relation of an apparatus for synthesizing radiopharmaceutical according to an embodiment of the present invention.

Referring to FIG. 1 to FIG. 3, an apparatus for synthesizing F-18 labeled radioactive pharmaceutical according to an embodiment of the present invention will be explained in detail hereinafter.

First, referring to FIG. 2, an F-18 radioactive isotope supplier 110 which supplies F-18 radioactive isotope is provided. For example, the F-18 radioactive isotope supplier 110 may be formed in a type of a tank within the body 20.

Meanwhile, a reagent supplier 120 which supplies a reagent reacting with the F-18 radioactive isotope is provided. A radioactive pharmaceutical is synthesized through processes of chemical reaction such as substitution and ion exchange of the F-18 radioactive isotope and the reagent and activation by heating or cooling or the like. The reagent supplied form the reagent supplier 120 may include some reagents which are needed for synthesis such as organic solvent.

A polymer precursor cartridge 130 which is filled with polymer cartridge may be provided. The polymer precursor cartridge 130 captures the F-18 radioactive isotope and causes a labeling reaction. For example, the polymer precursor may be a polymer precursor which is connected by quaternary ammonium salt. The polymer precursor cartridge 130 may smoothly perform the labeling reaction only using a small amount of precursor and may suppress generation of impurities during the reaction.

A first heating unit 140 which can selectively heat the polymer precursor cartridge 130 may be provided. For example, the first heating unit 140 may be realized as various devices such as an electric furnace, a micro-wave oven, and a resistance coil, and may be disposed in the vicinity of the polymer precursor cartridge 130 to be configured so as to be able to selectively heat the polymer precursor cartridge 130 by on/off operation thereof.

Meanwhile, a polymer compound cartridge 150 which is filled with a polymer compound may be provided. The polymer compound cartridge 150 plays a role of separating impurities from the final synthesized product by separating polar compound and nonpolar compound from each other. For example, the polymer compound may be C-18 polymer, polystyrene polymer, Hypercarb, HLB polymer, or the like.

A synthesizing container 160 which causes hydrolysis reaction of the produced intermediate compound may be provided. For example, the synthesizing container 160 may be connected to the polymer precursor cartridge 130 and the polymer compound cartridge 150 so as to store the produced compound and may cause the hydrolysis reaction of the intermediate compound therein.

A second heating unit 170 which can selectively heat the synthesizing container 160 is provided. For example, the second heating unit 170 may be realized as various devices such as an electric furnace, a micro-wave oven, and a resistance coil, and may be disposed in the vicinity of the synthesizing container 160 to be configured so as to be able to selectively heat the synthesizing container 160 by on/off operation thereof.

Heating of the synthesizing container 160 may cause a hydrolysis reaction of compound in the synthesizing container 160 to occur.

A waste fluid container 180 contains fluid which is discarded after having been used for synthesis. For example, the waste fluid container 180 is connected to the polymer precursor cartridge 130, the polymer compound cartridge 150, the synthesizing container 160, etc. so as to receive the discarded fluid which has been used to synthesis and stores the received fluid.

A collection container 190 collects the F-18 labeled radioactive pharmaceutical which is the final synthesized product. For example, the collection container 190 is connected to the polymer precursor 130 and the polymer compound cartridge 150 so as to be supplied with the final synthesized compound.

A transmitting gas supplier 210 which supplies gas for transmitting may be provided. The transmitting gas plays a role of pressing F-18 radioactive isotope or reagent to transmit the same, and also plays a role of cooling. For example, the transmitting gas supplier 210 may be realized as an air pump which is disposed in the body 20 and discharges pressurized air.

In addition, a cleansing liquid supplier 220 which supplies cleansing liquid may be provided. The cleansing liquid may pass through the polymer precursor cartridge 130 and the polymer compound cartridge 150 to clean the same. For example, the cleansing liquid may be distilled water. The cleansing liquid supplier 220 may be realized as a pump which is disposed in the body 20 and discharges liquid.

The reagent supplier 120 may be formed to be able to supply various reagents needed for the synthesis of the radioactive pharmaceutical.

For example, the reagent supplier 120 may includes a first organic solvent supplying unit 121 which supplies a first organic solvent for removing water within the polymer precursor cartridge 130, for the synthesis of the F-18 labeled radioactive pharmaceutical. For example, the first organic solvent may be acetonitrile ($CH_3CN$), dimethylformamide, dimethylsulfoxide, tertiary alcohol, or the like.

Meanwhile, the reagent supplier 120 may include a second organic solvent supplying unit 123 which supplies a second organic solvent which can be used as a reaction solvent for elution and deprotection of F-18 labeled compound produced within the polymer precursor cartridge 130. The second organic solvent may be an organic solvent containing acid or a mixed liquid of water and organic solvent. For example, the second organic solvent may be a mixed liquid of an acid containing hydrogen ion and methyl alcohol.

In addition, the reagent supplier 120 may include an alkaline aqueous solution supplying unit 125 which supplies an alkaline aqueous solution for neutralizing the synthesized liquid within the synthesizing container 160. For example, the alkaline aqueous solution may be any alkaline aqueous solution containing hydroxyl ion.

Further, the reagent supplier 120 may include a third organic solvent supplying unit 127 which supplies a third organic solvent for elution of F-18 labeled compound within the polymer compound cartridge 150. For example, the third organic solvent may be acetonitrile ($CH_3CN$), methanol, ethanol, dimethylsulfoxide, or the like.

Referring to FIG. 1 and FIG. 2, a plurality of connection portions a, b, c, d and e are provided to the cassette 10, and the cleansing liquid supplier 220, the first organic solvent supplying unit 121, the second organic solvent supplying unit 123, the alkaline aqueous solution supplying unit 125, and the third organic solvent supplying unit 127 are respectively connected to the connection portions a, b, c, d and e.

Meanwhile, a connection tube 11 which connects the above-described components together is provided. That is, the connection tube 11 connects the F-18 radioactive isotope supplier 110, the reagent supplier 120, the polymer precursor cartridge 130, the polymer compound cartridge 150, the synthesizing container 170, the waste liquid container 180, the collection container 190, the transmitting gas supplier 210, and the cleansing liquid supplier 220 together. F-18 radioactive isotope, reagent, transmitting gas, cleaning liquid can be transmitted to and supplied to the polymer precursor cartridge 130, the polymer compound cartridge 150, the synthesizing container 160 and the waster liquid container 180 through the connection tube 11, and the compound which is synthesized in the polymer precursor cartridge 150, the polymer compound cartridge 150, the synthesizing container 160 may be supplied to the collection container 190. Further, if necessary for the synthesis, F-18 radioactive isotope, transmitting gas, cleansing liquid can be supplied to the various components through the connection tube 11.

A plurality of control valves 13 are disposed at predetermined positions of the connection tube 11 and perform selective opening/closing operation. The control valves 13 control the flow of fluid such as F-18 radioactive isotope, transmitting gas, cleansing liquid, and reagent, through on/off operation thereof. For example, the control valves 13 may be 2-way valve which can open or close the connection tube 11 through on/off operation thereof.

A controller 30 which controls operations of the first heating unit 140, the second heating unit 170, and the control valves 13 is provided. Referring to FIG. 3, the controller 30 may be connected to the first heating unit 140, the second heating unit 170, and the control valves 13 so as to output control signals thereto. The controller 30 may include relevant hardware and software for performing this control, and may be configured to perform process for synthesizing radioactive pharmaceutical.

Further, a vacuum pump 40 which is connected to the waste container 180, the synthesizing container 160 and the collection container 190 to selectively form vacuum therein may be provided. The vacuum pump 40 provides power to transmit one or more of the F-18 radioactive isotope, the transmitting gas, the cleansing liquid, and the reagent, and vacuum is formed in the waster container 180, the synthesizing container 160 and the collection container 190 so that the F-18 radioactive isotope, the transmitting gas, the cleansing liquid, and the reagent can be transmitted. The vacuum pump 40 can be controlled by control signal of the controller 30.

The polymer precursor cartridge 130, the polymer compound cartridge 150, the connection tube 11, and the plurality of the control valves 13 may be formed as a type of the removeable cassette 10 so as to be selectively attached or detached. Accordingly, the cassette 10 including these components can be used as a disposable member and can be discarded after being used.

Some examples of processes of synthesis of radioactive pharmaceutical will be described. Such processes may be performed by control of operations of the first heating unit 140, the second heating unit 170, the control valves 13, and the vacuum pump 40 by the controller 30.

First, a first exemplary synthesizing process may includes making F-18 radioactive isotope pass through the polymer precursor cartridge 130 and then flow into the waste liquid container 180, making the transmitting gas pass through the polymer precursor cartridge 130 and then flow into the waster liquid container 180, making the cleaning liquid pass through the polymer precursor cartridge 130 and then flow into the waster liquid container 180, making the first organic solvent pass through the polymer precursor cartridge 130 and then flow into the waster liquid container 180, closing the connection tube 13 connected to the polymer precursor cartridge 130, heating the polymer precursor cartridge 130 using the first heating unit 140, making the transmitting gas pass through the polymer precursor cartridge 130 so as to cool the polymer precursor cartridge 130, making the second organic solvent pass through the polymer precursor cartridge 130 and then flow into the synthesizing container 160, heating the synthesizing container 160 using the second heating unit 170, making the alkaline liquid flow into the synthesizing container 160, making liquid within the synthesizing container 160 pass through the polymer compound cartridge 150 and then flow into the waste liquid container 180, making the cleansing liquid pass through the polymer compound cartridge 150 and then flow into the waste liquid container 180, making the transmitting gas pass through the polymer compound cartridge 150 and then flow into the waste liquid container 180, and making the third organic solvent pass through the polymer compound cartridge 150 and then flow into the collection container 190.

Next, a second exemplary synthesizing process may includes making F-18 radioactive isotope pass through the polymer precursor cartridge 130 and then flow into the waste liquid container 180, making the transmitting gas pass through the polymer precursor cartridge 130 and then flow into the waste liquid container 180, making the cleaning liquid pass through the polymer precursor cartridge 130 and then flow into the waster liquid container 180, making the first organic solvent pass through the polymer precursor cartridge 130 and then flow into the waster liquid container 180, closing the connection tube 13 connected to the polymer precursor cartridge 130, heating the polymer precursor cartridge 130 using the first heating unit 140, making the transmitting gas pass through the polymer precursor cartridge 130 so as to cool the polymer precursor cartridge 130, and making the third organic solvent pass through the polymer compound cartridge 150 and then flow into the collection container 190.

Next, a third exemplary synthesizing process may includes making F-18 radioactive isotope pass through the polymer precursor cartridge 130 and then flow into the waste liquid container 180, making the transmitting gas pass through the polymer precursor cartridge 130 and then flow into the waster liquid container 180, making the cleaning liquid pass through the polymer precursor cartridge 130 and then flow into the waster liquid container 180, making the first organic solvent pass through the polymer precursor cartridge 130 and then flow into the waster liquid container 180, closing the connection tube 13 connected to the polymer precursor cartridge 130, heating the polymer precursor cartridge 130 using the first heating unit 140, making the transmitting gas pass through the polymer precursor cartridge 130 so as to cool the polymer precursor cartridge 130, making the second organic solvent sequentially pass through the polymer precursor cartridge 130 and the polymer compound cartridge 150 and then flow into the synthesizing container 160, making the transmitting gas sequentially pass through the polymer precursor cartridge 130 and the polymer compound cartridge 150 and then flow into the waste liquid container 180, and making the third organic solvent pass through the polymer compound cartridge 150 and then flow into the collection container 190.

According to the present invention, the synthesis of the radioactive pharmaceutical can be automatically performed by a single apparatus, and the synthesis of various radioactive pharmaceuticals can be performed by exchange of the cassette 10, and since all steps for synthesizing radioactive pharmaceutical can be performed by a single apparatus and it can be performed by remote control, monitoring and operation through ethernet communication, the worker can be protected from radiation exposure.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

INDUSTRIAL APPLICABILITY

The present invention can be applied to a device for manufacturing medicine, so it has an industrial applicability.

The invention claimed is:

1. An apparatus for synthesizing an F-18 labeled radioactive pharmaceutical by labeling a precursor of a pharmaceutical with an F-18 radioactive isotope to provide an F-18 labeled precursor, by reacting the F-18 labeled precursor to obtain a crude F-18 labeled pharmaceutical, by separating impurities from the crude F-18 labeled pharmaceutical to provide a purified F-18 labeled pharmaceutical, and by collecting the purified F-18 labeled pharmaceutical, the apparatus comprising:
   an F-18 radioactive isotope supplier which supplies an F-18 radioactive isotope;
   a reagent supplier which supplies at least one reagent;
   a labeling cartridge that contains the precursor, that receives the F-18 radioactive isotope, and that causes a labeling reaction to provide the F-18 labeled precursor;
   a first heating unit that selectively heats the labeling cartridge;
   a synthesizing container that receives the F-18 precursor, that receives at least one reagent effective to hydrolyze the F-18 labeled precursor, and within which the F-18 labeled precursor undergoes a hydrolysis reaction to provide the F-18 labeled pharmaceutical;
   a second heating unit which selectively heats the synthesizing container;
   a separation cartridge that receives the F-18 labeled pharmaceutical, and that contains a polymer compound that separates impurities into polar compounds and nonpolar compounds to provide a purified F-18 labeled pharmaceutical;
   a waste liquid container which receives and contains fluid which is discarded after synthesis;
   a collecting container which collects the F-18 labeled pharmaceutical from the separation cartridge;
   a transmitting gas supplier which supplies a flow of transmitting gas;
   a cleansing liquid supplier which supplies a cleansing liquid;
   a connection tube which connects the F-18 radioactive isotope supplier, the reagent supplier, the labeling cartridge, the separation cartridge, the synthesizing container, the waste liquid container, the collection container, the transmitting gas supplier, and the cleansing liquid supplier together;
   a plurality of control valves which are disposed at predetermined positions of the connection tube to perform selective opening and closing operations; and
   a controller which controls operations of the first heating unit, the second heating unit, and the plurality of the control valves.

2. The apparatus of claim 1, wherein the reagent supplier comprises:
   a first organic solvent supplying unit which supplies a first organic solvent for removing water from within the labeling cartridge;
   a second organic solvent supplying unit which supplies a second organic solvent which is an organic solvent containing acid or a mixed liquid of water and organic solvent for use as said at least one reagent effective to hydrolyze the F-18 labeled precursor;
   an alkaline aqueous solution supplying unit which supplies an alkaline aqueous solution for neutralizing synthesized liquid within the synthesizing container; and
   a third organic solvent supplying unit which supplies a third organic solvent for elution of the F-18 labeled pharmaceutical within the separation cartridge.

3. The apparatus of claim 1, wherein the precursor has a quarternary ammonium salt connected thereto.

4. The apparatus of claim 1, further comprising a vacuum pump which is connected to the waste container, the synthesizing container and the collection container to selectively form a vacuum therein for flowing one or more of the F-18 radioactive isotope, the transmitting gas, the cleansing liquid, and at least one of the at least one reagent.

5. The apparatus of claim 1, wherein the labeling cartridge, the separation cartridge, the connection tube, and the plurality of control valves are formed in a type of a removable cassette which can be selectively attached or detached.

6. The apparatus of claim 2, wherein the controller controls the plurality of control valves, the first heating unit, and the second heating unit so as to sequentially perform:
- making F-18 radioactive isotope pass through the labeling cartridge and then flow into the waste liquid container;
- making the transmitting gas pass through the labeling cartridge and then flow into the waster liquid container;
- making the cleaning liquid pass through the labeling cartridge and then flow into the waster liquid container;
- making the first organic solvent pass through the labeling cartridge and then flow into the waster liquid container;
- closing the connection tube connected to the labeling cartridge;
- heating the labeling cartridge using the first heating unit;
- making the transmitting gas pass through the labeling cartridge so as to cool the labeling cartridge;
- making the second organic solvent pass through the labeling cartridge and then flow into the synthesizing container;
- heating the synthesizing container using the second heating unit;
- making the alkaline aqueous solution flow into the synthesizing container;
- making liquid within the synthesizing container pass through the separation cartridge and then flow into the waste liquid container;
- making the cleansing liquid pass through the separation cartridge and then flow into the waste liquid container;
- making the transmitting gas pass through the separation cartridge and then flow into the waste liquid container; and
- making the third organic solvent pass through the separation cartridge and then flow into the collection container.

7. The apparatus of claim 2, wherein the controller controls the plurality of the control valves and the first heating unit so as to sequentially perform:
- making F-18 radioactive isotope pass through the labeling cartridge and then flow into the waste liquid container;
- making the transmitting gas pass through the labeling cartridge and then flow into the water liquid container;
- making the cleaning liquid pass through the labeling cartridge and then flow into the water liquid container;
- making the first organic solvent pass through the labeling cartridge and then flow into the water liquid container;
- closing the connection tube connected to the labeling cartridge;
- heating the polymer precursor cartridge using the first heating unit;
- making the transmitting gas pass through the labeling cartridge so as to cool the polymer precursor cartridge; and
- making the third organic solvent pass through the separation cartridge and then flow into the collection container.

8. The apparatus of claim 2, wherein the controller controls the plurality of control valves, the first heating unit, and the second heating unit so as to sequentially perform:
- making F-18 radioactive isotope pass through the labeling cartridge and then flow into the waste liquid container;
- making the transmitting gas pass through the labeling precursor cartridge and then flow into the water liquid container;
- making the cleaning liquid pass through the labeling cartridge and then flow into the water liquid container;
- making the first organic solvent pass through the labeling cartridge and then flow into the waster liquid container;
- closing the connection tube connected to the labeling cartridge;
- heating the labeling cartridge using the first heating unit;
- making the transmitting gas pass through the labeling cartridge so as to cool the labeling cartridge;
- making the second organic solvent sequentially pass through the labeling cartridge and the separation cartridge and then flow into the synthesizing container;
- making the transmitting gas sequentially pass through the labeling cartridge and the separation cartridge and then flow into the waste liquid container; and
- making the third organic solvent pass through the separation cartridge and then flow into the collection container.

9. A method for a synthesizing a radioactive pharmaceutical using the apparatus according to claim 1, the method comprising:
- making F-18 radioactive isotope pass through the labeling cartridge and then flow into the waste liquid container;
- making the transmitting gas pass through the labeling cartridge and then flow into the waste liquid container;
- making the cleaning liquid pass through the labeling cartridge and then flow into the waste liquid container;
- making the first organic solvent pass through the labeling cartridge and then flow into the waste liquid container;
- closing the connection tube connected to the labeling cartridge;
- heating the labeling cartridge using the first heating unit;
- making the transmitting gas pass through the labeling precursor cartridge so as to cool the labeling cartridge;
- making the second organic solvent pass through the labeling cartridge and then flow into the synthesizing container;
- heating the synthesizing container using the second heating unit;
- making the alkaline aqueous solution flow into the synthesizing container;
- making liquid within the synthesizing container pass through the separation cartridge and then flow into the waste liquid container;
- making the cleansing liquid pass through the separation cartridge and then flow into the waste liquid container;
- making the transmitting gas pass through the separation cartridge and then flow into the waste liquid container; and
- making the third organic solvent pass through the separation cartridge and then flow into the collection container.

10. A method for synthesizing a radioactive pharmaceutical using the apparatus according to claim 1, the method comprising:
- making F-18 radioactive isotope pass through the labeling cartridge and then flow into the waste liquid container;
- making the transmitting gas pass through the labeling cartridge and then flow into the waste liquid container;
- making the cleaning liquid pass through the labeling cartridge and then flow into the waste liquid container;
- making the first organic solvent pass through the labeling cartridge and then flow into the waste liquid container;
- closing the connection tube connected to the labeling cartridge;
- heating the labeling cartridge using the first heating unit;
- making the transmitting gas pass through the labeling cartridge so as to cool the labeling cartridge; and
- making the third organic solvent pass through the separation cartridge and then flow into the collection container.

11. A method for a synthesizing radioactive pharmaceutical using the apparatus according to claim 1, the method comprising:
making F-18 radioactive isotope pass through the polymer precursor cartridge and then flow into the waste liquid container;
making the transmitting gas pass through the polymer precursor cartridge and then flow into the waster liquid container;
making the cleaning liquid pass through the polymer precursor cartridge and then flow into the waster liquid container;
making the first organic solvent pass through the polymer precursor cartridge and then flow into the waster liquid container;
closing the connection tube connected to the polymer precursor cartridge;
heating the polymer precursor cartridge using the first heating unit;
making the transmitting gas pass through the polymer precursor cartridge so as to cool the polymer precursor cartridge;
making the second organic solvent sequentially pass through the polymer precursor cartridge and the separation cartridge and then flow into the synthesizing container;
making the transmitting gas sequentially pass through the polymer precursor cartridge and the separation cartridge and then flow into the waste liquid container; and
making the third organic solvent pass through the separation cartridge and then flow into the collection container.

12. The apparatus of claim 2, further comprising a vacuum pump which is connected to the waste container, the synthesizing container and the collection container to selectively form a vacuum therein for flowing one or more of the F-18 radioactive isotope, the transmitting gas, the cleansing liquid, and at least one of the at least one reagent.

13. The apparatus of claim 3, further comprising a vacuum pump which is connected to the waste container, the synthesizing container and the collection container to selectively form a vacuum therein for flowing one or more of the F-18 radioactive isotope, the transmitting gas, the cleansing liquid, and at least one of the at least one reagent.

14. The apparatus of claim 2, wherein the first organic solvent for removing water from within the labeling cartridge is selected from the group consisting of acetonitrile ($CH_3CN$), dimethylformamide, dimethylsulfoxide, and a tertiary alcohol.

15. The apparatus of claim 2, wherein the second organic solvent is a mixed liquid of an acid containing hydrogen ion and methyl alcohol.

16. The apparatus of claim 2, wherein the third organic solvent is acetonitrile ($CH_3CN$), methanol, ethanol, and dimethylsulfoxide.

17. The apparatus of claim 1, wherein the polymer compound contained in the separation cartridge is selected from the group consisting of C-18™ polymer, a polystyrene polymer, Hypercarb™, and a HLB polymer.

* * * * *